US00PP10523P

United States Patent [19]

Stahnke et al.

[11] Patent Number: Plant 10,523

[45] Date of Patent: Jul. 28, 1998

[54] AZALEA PLANT NAMED 'THEO'

[76] Inventors: Otto Stahnke; Peter Dettmer; Eleonore Dettmer, all of Bromer Strasse 104, 38524 Sassenburg-Grussendorf, Germany

[21] Appl. No.: 802,236

[22] Filed: Feb. 19, 1997

[51] Int. Cl.[6] ..... A01H 5/00

[52] U.S. Cl. ..... Plt./56

[58] Field of Search ..... Plt./56

[56] References Cited

PUBLICATIONS

Plant Varieties Journal 7(4):31, Dec. 1994.

*Primary Examiner*—Elizabeth C. Kemmerer
*Attorney, Agent, or Firm*—C. A. Whealy

[57] ABSTRACT

A new and distinct cultivar of Azalea plant named 'Theo', characterized by its uniform and freely branching plant habit; durable and glossy leaves; attractive semi-double, pink-colored flowers with dark purple speckled centers; and good postproduction longevity.

2 Drawing Sheets

SUMMARY OF THE INVENTION

The present invention relates to a new and distinct cultivar of Azalea, botanically known as *Rhododendron simsii*, and hereinafter referred to by the cultivar name 'Theo'.

The new cultivar is a product of a planned breeding program conducted by the inventors in Sassenburg-Grussendorf, Germany. The objective of the breeding program is to create new Azalea cultivars that are durable and have inflorescences with desirable flower colors and uniform plant habit. The new cultivar originated from a cross made by the inventors of an unnamed proprietary seedling selection as the male, or pollen, parent with the commercial cultivar 'Oslo' (not patented) as the female, or seed, parent. The cultivar 'Theo' was discovered and selected by the inventors as a flowering plant within the progeny of the stated cross in a controlled environment in Sassenburg-Grussendorf, Germany.

Compared to plants of the male parent, a proprietary seedling selection with pink-colored flowers, plants of the new Azalea have more durable foliage, more intense pink flower color, flower earlier, and are less susceptible to diseases. Compared to plants of the female parent, the cultivar 'Oslo', plants of the new Azalea have more vigorous and stronger root and plant growth, more durable foliage, more intense flower color, and flower four to six weeks earlier.

Asexual reproduction of the new cultivar by terminal cuttings taken at Sassenburg-Grussendorf, Germany, has shown that the unique features of this new Azalea plant are stable and reproduced true to type in successive generations of asexual reproduction.

The following traits have been repeatedly observed and are determined to be the unique characteristics of 'Theo'. These characteristics in combination distinguish the new Azalea plant as a new and distinct cultivar:

1. Uniform plant habit.
2. Very freely branching.
3. Durable and glossy leaves.
4. Attractive semi-double, pink-colored flowers with dark purple speckled centers.
5. Good postproduction longevity with plants maintaining flowers for about four weeks.

Plants of the new Azalea can be compared to plants of the cultivar 'Rosali' (not patented). However in side-by-side comparisons in Sassenburg-Grussendorf, Germany, under commercial practice, plants of the new Azalea have more intense flower color, are more vigorous, flower earlier and are less susceptible to diseases than plants of the cultivar 'Rosali'.

The new Azalea plant has not been observed under all possible environmental conditions. The phenotype may vary significantly with variations in environment such as temperature, light level, nutrition and water status without, however, any variance in genotype.

BRIEF DESCRIPTION OF THE DRAWINGS

The accompanying colored photographs illustrate the overall appearance of the new cultivar, showing the colors as true as it is reasonably possible to obtain in colored reproductions of this type.

The first photograph comprises a side perspective view of typical plant of 'Theo'.

The second photograph comprises a close-up view of a typical flowers of 'Theo'.

Flower and foliage colors in the photographs may appear different from the actual colors due to light reflectance.

DETAILED DESCRIPTION OF THE INVENTION

The following observations, measurements, values, and comparisons describe plants grown in Salinas, Calif., in 12.5-cm containers under glass with day temperatures ranging from 24° to 27° C., night temperatures ranging from 13° to 16° C., and light levels averaging 4,500 footcandles.

In the following description, color references are made to The Royal Horticultural Society Colour Chart except where general terms of ordinary dictionary significance are used.

Classification:

*Botanical.*—*Rhododendron simsii* cv. 'Theo'.

Parentage:

*Male or pollen parent.*—Unnamed proprietary *Rhododendron simsii* seedling selection with pink-colored flowers.

*Female or seed parent.*—*Rhododendron simsii* cv. 'Oslo' (not patented).

Propagation:

*Type.*—By terminal cuttings.

*Time to initiate roots.*—About 23 days at temperatures of 22° C.

*Rooting habit.*—Strong roots, vigorous and finely-branched.

Plant description:

*Plant form and growth habit.*—Perennial, evergreen, upright and outwardly arching, inverted triangle. Moderate vigor.

*Branching habit.*—Dense, very freely branching, about five lateral branches develop after removal of terminal apex.

*Plant height, soil level to top of flowers.*—About 16.5 cm.

*Plant diameter, area of spread.*—About 27 cm.

*Lateral branch description.*—Length: About 10 cm. Diameter: About 5 mm. Color: Immature: 145A. Mature: 175B. Texture: Moderately pubescent.

Foliage description:

*Arrangement.*—Alternate, single.

*Leaf size, largest leaves.*—Length: About 4 cm. Width: About 2.2 cm.

*Leaf shape.*—Elliptic to obovate.

*Leaf apex.*—Acute.

*Leaf base.*—Cuneate.

*Margin type.*—Entire.

*Texture.*—Durable, leathery, very glossy, both surfaces pubescent.

*Color.*—Young foliage, abaxial surface: Greener than 137A. Young foliage, adaxial surface: 138B. Mature foliage, abaxial surface: 137A. Mature foliage, adaxial surface: 138B.

*Petiole.*—Length: About 9 mm. Diameter: About 2 mm. Color: 138B.

Flower description:

*Natural flowering season.*—Spring after sufficient cool period. F

*Flower arrangement.*—Flowers arranged singly at terminals with usually three to five flowers per terminal. Flowers face upward and outward. Freely flowering.

*Flower appearance.*—Star-shaped semi-double. Pink-colored petals with dark purple-speckled centers. Flowers persistent.

*Flower diameter.*—About 8 cm.

*Flower longevity.*—Six to eight days depending on temperature.

*Flower bud.*—Rate of opening: About three days depending on temperatures. Length: About 2.5 cm. Diameter: About 1 cm. Shape: Ovoid. Color: 65C.

*Petals.*—Appearance: Satiny, smooth. Texture: Glabrous. Arrangement: Semi-double. Outer corolla consists of five fused petals and inner corolla consists of up to 5 irregularly-shaped fused stamenoidal petaloids. Shape: Elliptic with rounded apex. Margin: Entire with slight ruffling. Size: Length: About 4.2 cm. Width: About 3.2 cm. Color: When opening, abaxial surface: 65A with speckles, 58B, at base of lower three petals. When opening, adaxial surface: 65C. Fully opened, abaxial surface: Iridescent, 68A at edges, 62B at center, with speckles, 58B, at base of lower three petals. Over time, petal color becomes uniformly 62B with speckles, 58B, at base of lower three petals. Fully opened, adaxial surface: 68B fading to 155D at base.

*Sepals.*—Appearance: Five sepals fused into a star-shaped calyx. Texture: Very pubescent. Shape: Elliptic. Apex: Rounded. Margin: Entire. Color, abaxial and adaxial surfaces: 146B.

*Peduncles.*—Length: About 2 cm. Angle: Upright. Strength: Rigid. Color: 145A, pubescent.

*Reproductive organs.*—Androecium: Stamen number: Five to ten, usually fused into petaloids. Anther shape: Oblong. Anther size: About 2 mm. Anther color: Dark pink. Amount of pollen: Moderate. Pollen color: Golden orange. Gynoecium: Pistil number: One. Pistil length: About 3.5 cm. Stigma shape: Rounded. Stigma diameter: About 2 mm. Stigma color: Green becoming yellow with development. Style length: About 3 cm. Style color: White to light pink. Ovary color: Green.

Disease resistance: No known Azalea diseases observed to date on plants grown under commercial greenhouse conditions. Plants of the new Azalea appear to be less susceptible to diseases than other commercial cultivars.

Seed production: Seed production has not been observed.

It is claimed:

1. A new and distinct Azalea plant named 'Theo', as illustrated and described.

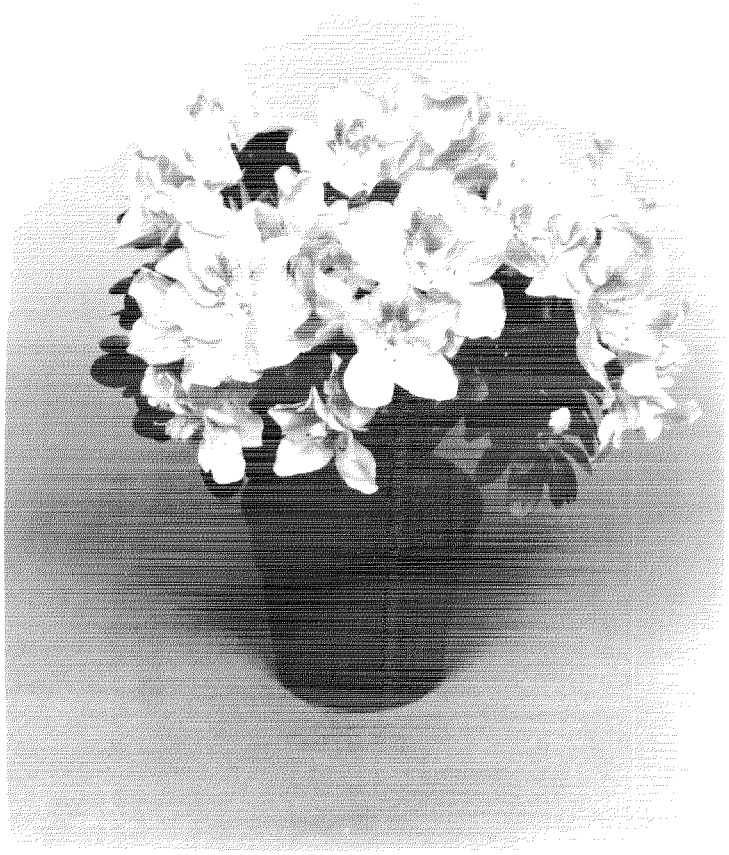

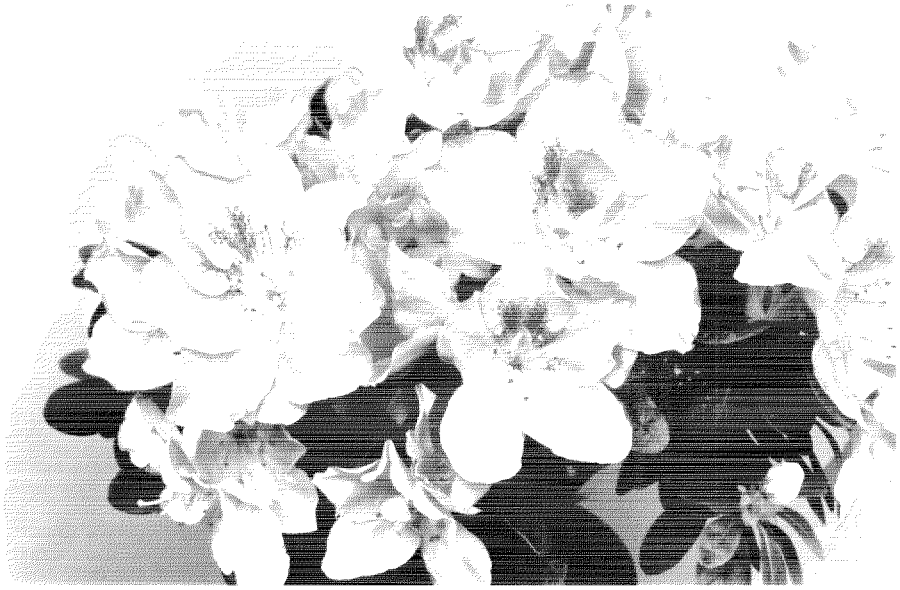

* * * * *